United States Patent
Bush

(10) Patent No.: US 7,735,513 B2
(45) Date of Patent: Jun. 15, 2010

(54) DIAPHRAGM VALVE WITH ELECTRONIC PRESSURE DETECTION

(75) Inventor: Shawn D. Bush, Orlando, FL (US)

(73) Assignee: I-CON Systems, Inc., Oviedo, FL (US)

( * ) Notice: Subject to any disclaimer, the term of this patent is extended or adjusted under 35 U.S.C. 154(b) by 417 days.

(21) Appl. No.: 11/246,332

(22) Filed: Oct. 7, 2005

(65) Prior Publication Data

US 2006/0076061 A1 Apr. 13, 2006

Related U.S. Application Data

(60) Provisional application No. 60/617,264, filed on Oct. 8, 2004.

(51) Int. Cl.
*F16K 31/385* (2006.01)
(52) U.S. Cl. .............. 137/489.5; 251/30.05; 137/492
(58) Field of Classification Search .......... 137/489.5, 137/487.5, 489, 492.5, 557, 492; 251/30.01–30.05; 335/219; 73/714
See application file for complete search history.

(56) References Cited

U.S. PATENT DOCUMENTS

| | | | |
|---|---|---|---|
| 4,301,992 A | 11/1981 | Karbo | |
| 4,336,918 A | 6/1982 | Karbo | |
| 4,477,051 A | 10/1984 | Ben-Yehuda | |
| 4,787,413 A | 11/1988 | Saggers | |
| 4,797,820 A | 1/1989 | Wilson et al. | |
| 4,893,645 A | 1/1990 | Augustinas et al. | |
| 5,125,621 A * | 6/1992 | Parsons et al. | 251/30.03 |
| 5,438,714 A | 8/1995 | Shaw | |
| 5,853,026 A | 12/1998 | Wlodarczyk et al. | |
| 6,189,563 B1 * | 2/2001 | Taylor | 137/487.5 |
| 6,557,580 B2 | 5/2003 | Lohde et al. | |
| 6,715,506 B1 * | 4/2004 | Ikushima | 137/14 |
| 2002/0167220 A1 * | 11/2002 | Cunkelman | 303/128 |
| 2003/0010390 A1 * | 1/2003 | Beck et al. | 137/884 |
| 2003/0148018 A1 * | 8/2003 | Hoffmann et al. | 427/8 |
| 2006/0076527 A1 | 4/2006 | Bush | |

* cited by examiner

*Primary Examiner*—John Rivell
*Assistant Examiner*—William McCalister
(74) *Attorney, Agent, or Firm*—The Webb Law Firm

(57) ABSTRACT

A flush valve for a waste water system comprises a valve including a fluid inlet, a fluid outlet and a main valve element adapted for movement to allow fluid flow between the fluid inlet and the fluid outlet based on a pressure differential across a portion of the main valve element. The valve also includes a vent system comprising a control chamber in flow communication with the fluid inlet of the valve and a vent outlet in flow communication with the fluid outlet of the valve, and a solenoid for venting fluid venting fluid from the control chamber to the fluid outlet. A pressure sensor, such as an electronic pressure transducer, senses the fluid pressure of fluid within the vent system. When a predetermined pressure threshold is reached or exceeded, the solenoid can be energized to release fluid from the control chamber.

12 Claims, 9 Drawing Sheets

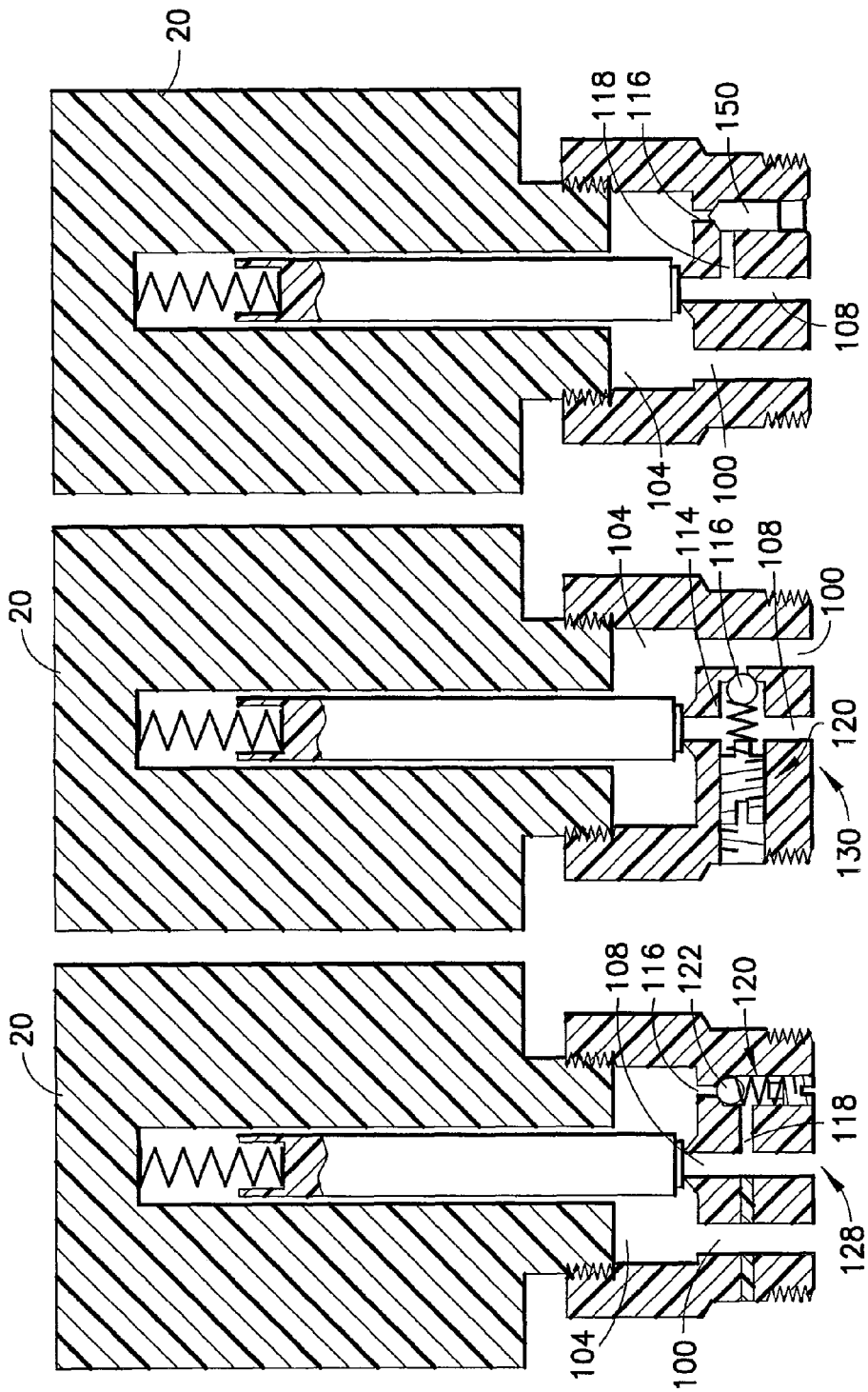

DIAPHRAGM VALVE WITH ELECTRONIC PRESSURE DETECTION

CROSS REFERENCE TO RELATED APPLICATIONS

This application claims the benefits of U.S. Provisional Application Ser. No. 60/617,264, filed Oct. 8, 2004, herein incorporated by reference in its entirety.

This application is related to U.S. application Ser. No. 11/246,457 entitled "Method For Modifying A Plastic Body Valve For Use In A Waste Water System" and U.S. application Ser. No. 11/246,456 entitled "Diaphragm Valve With Mechanical Pressure Relief", both filed concurrently herewith, and both herein incorporated by reference in their entirety.

BACKGROUND OF THE INVENTION

1. Field of the Invention

This invention relates generally to diaphragm valves and, in one particular embodiment, to a plastic body diaphragm valve having a pressure relief for use as a flush valve in a waste water system.

2. Technical Considerations

In most waste water systems, such as the flushing systems for urinals, commodes, and the like, the valves associated with these systems are traditionally metal valves. Metal valves provide strength for withstanding high-pressure fluctuations that may occur in the water pressure of the flushing system and also maintain their ability to function over prolonged and consistent use. However, these traditional metal flush valves do have some drawbacks. For example, these metal valves are typically relatively heavy and cumbersome to install and repair. Moreover, with continued use, metal valves may corrode or rust, and/or develop mineral deposits, which can require replacement of the entire valve. Additionally, such metal valves are typically expensive to manufacture and maintain.

Plastic valves are generally lighter in weight and less costly than metal valves and eliminate the corrosion associated with metal valves while reducing the development of mineral deposits. However, plastic valves are typically not as strong as metal valves. That is, plastic valves cannot typically withstand as high fluid pressures as metal valves without leaking or breaking. While plastic valves do exist, these known plastic valves are not capable of meeting the American Society Of Sanitary Engineering (ASSE) requirements for use in conventional waste water systems. For example, one ASSE requirement is that the valves in the waste water system must not leak at a fluid pressure of 500 psi or, if the valve incorporates a relief valve, the valve must hold two-times the relief pressure without leaking. Conventional plastic bodied valves cannot meet these limitations.

Additionally, many modern commodes and/or urinals are designed to operate most efficiently using a standard amount of water per flush, typically in the range of 1.5 to 2 gallons per flush. Therefore, known metal flush valves are designed to provide a selected amount of water per flush when new. However, with continued or prolonged use over time or as the internal components of the metal valve wear, it is not uncommon for these known metal flush valves to provide a different amount of water per flush than they were originally designed to provide. For example, a metal flush valve originally designed to provide 1.6 gallons per flush when new may eventually provide 2 or more gallons per flush due to valve component wear or use. For large applications, such as hospitals, prisons, apartment buildings, and the like, this can lead to an increase in water usage and cost. Additionally, these known flush valves cannot compensate for variations in water pressure during the flushing cycle that can also affect the amount of water per flush the valve provides.

Therefore, it would be advantageous to provide a flush valve that reduces or eliminates at least some of the problems associated with known flush valves. For example, it would be advantageous to provide a plastic body flush valve with a relief system that meets current ASSE requirement. It would likewise be advantageous to provide a flush valve that can provide a predetermined amount of water per flush despite valve wear and/or water pressure fluctuations.

SUMMARY OF THE INVENTION

A flush valve for a waste water system comprises a valve including a fluid inlet, a fluid outlet and a main valve element extending between the fluid inlet and the fluid outlet, with the main valve element adapted for movement to allow fluid flow between the fluid inlet and the fluid outlet based on a pressure differential across a portion of the main valve element. The valve also includes a vent system comprising a control chamber in flow communication with the fluid inlet of the valve and a vent outlet in flow communication with the fluid outlet of the valve. The valve further includes a solenoid including a piston configured to open to establish flow communication between the control chamber and the vent outlet for venting fluid from the control chamber to the fluid outlet and establishing a pressure differential across a portion of the main valve element to open the main valve element for fluid flow between the fluid inlet and fluid outlet of the valve. The piston is also configured to close to prevent fluid communication between the control chamber and the vent outlet to close the main valve element. The valve also comprises a pressure sensor, such as an electronic pressure transducer, adapted to sense the fluid pressure of fluid within the vent system. The pressure sensor can regulate the internal pressure within the valve to prevent leakage and/or damage of the valve based on excessive pressure therein, and is therefore particularly useful with valves where least a portion of the valve body is constructed of a plastic material.

The vent system may include a vent chamber in flow communication with the control chamber through a vent inlet passage extending between the control chamber and the vent chamber, with the vent outlet is in flow communication with the vent chamber. Moreover, the solenoid may include a core tube in which the piston is slidable, with the core tube in flow communication with the vent chamber, and with an actuating coil around at least a portion of the core tube. In such an embodiment, the pressure sensor can extend into the core tube.

A method of controlling a flush valve comprises provided such as flush valve, defining a pressure threshold corresponding to a relief pressure for the valve, sensing the fluid pressure of fluid within the valve, and activating the solenoid when the fluid pressure within the valve meets or exceeds the defined pressure threshold.

In a further embodiment, a method of regulating pressure within a flush valve in a waste water system comprises providing a valve including a fluid inlet, a fluid outlet and a main valve element adapted for movement to allow fluid flow between the fluid inlet and the fluid outlet based on a pressure differential across a portion of the main valve element. The valve further comprises a vent system for venting fluid from the fluid inlet to the fluid outlet to establish a pressure differential across a portion of the main valve element to cause the main valve element to open. In the method, the fluid pressure of fluid within the vent system of the valve is sensed. Fluid within the vent system of the valve is vented from the fluid inlet to the fluid outlet when the fluid pressure within the vent system exceeds a predetermined pressure threshold corresponding to a relief pressure for the valve.

Desirably, the vent system comprises a control chamber in flow communication with the fluid inlet of the valve, a vent outlet in flow communication with the fluid outlet of the valve, and an electronically operated solenoid having a piston configured to open and close the vent outlet upon energization thereof. In such an embodiment, the venting step comprises energizing the solenoid to open the vent outlet to establish flow communication between the control chamber and the vent outlet to vent fluid from the control chamber to the fluid outlet. The solenoid may be energized for a predetermined period of time. Desirably, the solenoid is energized for a period of time below that required to vent a volume of fluid from the vent chamber associated with establishing a pressure differential across a portion of the main valve element which would cause the main valve element to open. In this manner, the fluid pressure within the vent chamber can be reduced below a threshold level without opening the main valve element.

A voltage threshold may further be defined, corresponding to the predetermined pressure threshold for the valve. In this manner, the solenoid can be energized when the voltage threshold is detected. Moreover, a closing voltage threshold corresponding to a pressure value below the predetermined pressure threshold for the valve may also be defined. As such, the solenoid can be de-energized when the closing voltage threshold is attained.

In a further embodiment, a method of operating a flush valve in a waste water system comprises providing a valve including a fluid inlet, a fluid outlet and a main valve element adapted for movement to allow fluid flow between the fluid inlet and the fluid outlet based on a pressure differential across a portion of the main valve element. The valve comprises a vent system for venting fluid from the fluid inlet to the fluid outlet to establish a pressure differential across a portion of the main valve element to cause the main valve element to open, with the vent system comprising a control chamber in flow communication with the fluid inlet of the valve, a vent outlet in flow communication with the fluid outlet of the valve, and an electronically operated solenoid. The solenoid includes a piston configured to open the vent outlet upon energization thereof to establish flow communication between the control chamber and the vent outlet to vent fluid from the control chamber to the fluid outlet, and to close the vent outlet upon de-energization thereof. Operation of the valve involves sensing the static fluid pressure of fluid within the vent system, calculating a valve operation time associated with delivering a predetermined quantity of water through the valve based on the static fluid pressure, and energizing the solenoid for a time period associated with the valve operation time. Desirably, the predetermined quantity of water is 1.6 gallons, thereby effecting flushing of a toilet fixture associated with the valve.

The method may further comprise monitoring the dynamic fluid pressure of fluid within the vent system during the valve operation, and adjusting the time period of energization of the solenoid based on the dynamic fluid pressure to regulate the valve operation time.

BRIEF DESCRIPTION OF THE DRAWINGS

Additional advantages and details of the invention are explained in greater detail below with reference to the exemplary embodiments that are illustrated in the accompanying schematic figures, in which:

FIGS. 7-9 are side, cut-away views of valve portions similar to FIG. 3 but incorporating alternative valve relief systems;

DESCRIPTION OF THE PREFERRED EMBODIMENTS

Figure 1:
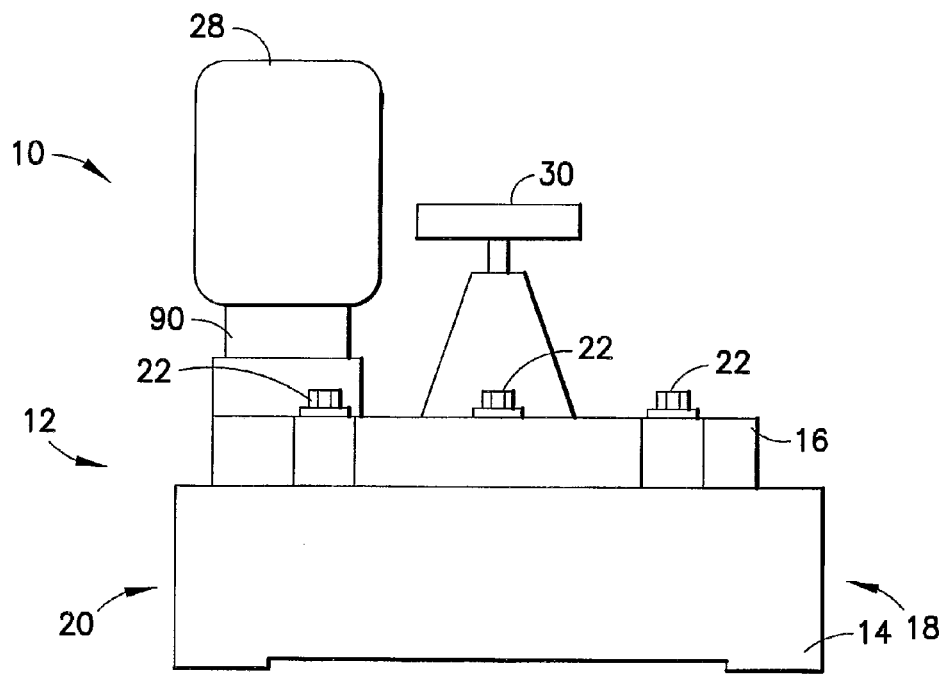
FIG. 1 is a side view of a plastic bodied valve incorporating features of the invention.
Figure 2:
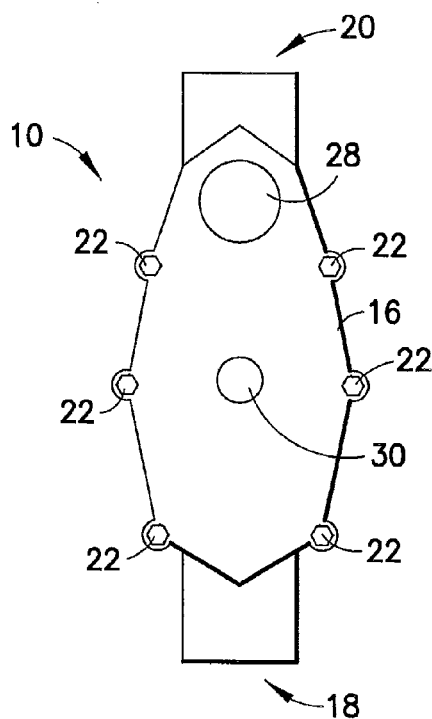
FIG. 2 is a top view of the valve of FIG. 1.
Figure 3:
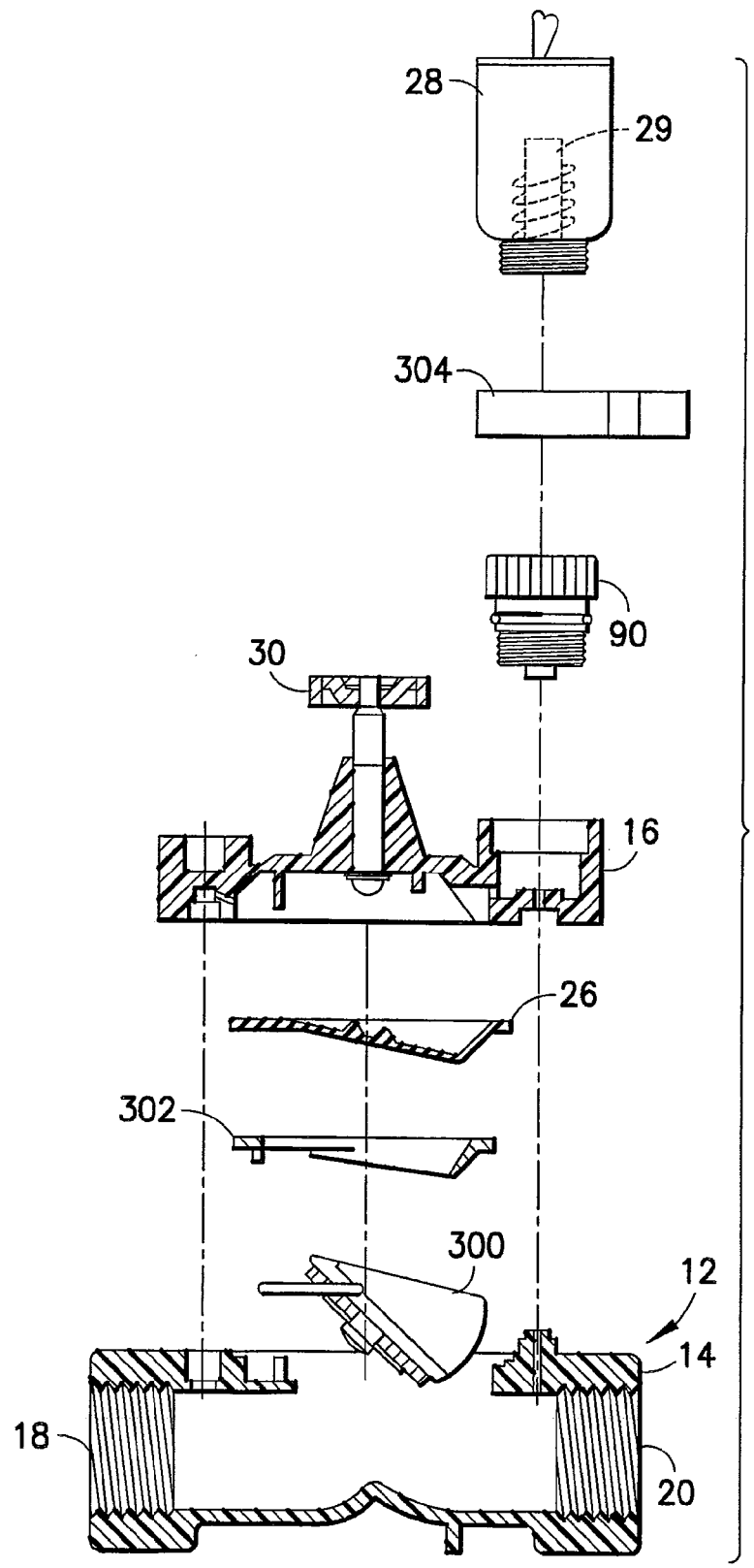
FIG. 3 is an exploded view of the valve of FIG. 1.

As used herein, spatial or directional terms, such as "up", "down", "above", "below", "top", "bottom", and the like, relate to the invention as it is shown in the drawing figures. However, it is to be understood that the invention can assume various alternative orientations and, accordingly, such terms are not to be considered as limiting. Further, all numbers expressing dimensions, physical characteristics, processing parameters, quantities of ingredients, reaction conditions, and the like, used in the specification and claims are to be understood as being modified in all instances by the term "about". Accordingly, unless indicated to the contrary, the numerical values set forth in the following specification and claims are approximations that can vary depending upon the desired properties sought to be obtained by the present invention. At the very least, and not as an attempt to limit the application of the doctrine of equivalents to the scope of the claims, each numerical value should at least be construed in light of the number of reported significant digits and by applying ordinary rounding techniques. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, e.g., 1 to 6.1, 3.5 to 7.8, 5.5 to 10, etc. All references referred to herein, such as but not limited to issued patents and published applications, are to be understood to be incorporated by reference in their entirety. The term "mechanical relief" refers to a relief device or system that does not require electricity or electrical power to function in a pressure relieving capacity. The term "electronic relief" refers to a relief device or system that utilizes electricity or electrical power to function in a pressure relieving capacity.

FIGS. 1-5 show a valve 10 of the present invention. The basic components of the valve 10 will first be described in order to clarify the subsequent discussion of the invention.

In one non-limiting embodiment, the valve 10 can be a diaphragm-type valve having a valve housing 12 formed by a valve body 14 and a cover 16. The valve body 14 and/or cover 16 can be of any desired material, for example, metal or plastic. In one non-limiting embodiment, the valve body 14 and cover 16 can both be made of plastic or one can be plastic and the other metal. The valve body 14 has a flow passage extending therethrough with an inlet end 18 and an outlet end 20. The cover 16 is connected to the valve body 14 by a plurality of bolts 22, such as aluminum or stainless steel bolts, threadably engagable with insert nuts 24 in the valve body 14. The insert nuts 24 can also be metal, such as brass or, more preferably, steel. A diaphragm 26 of suitable material, such as rubber or plastic, is sandwiched between the valve body 14 and the cover 16 to form a seal between the two chambers of the valve 10. A valve element 300 is positioned in the flow passage and the upper side of the valve element 300 engages the central region of the diaphragm 26 when the valve 10 is assembled. In one embodiment, the valve element 300 is a conventional swing check valve. The valve 10 further includes a solenoid 28 threadably attached to the cover 16 and operationally connected with a vent system to control water pressure in a control chamber formed above the diaphragm 26, as is typical in known diaphragm valves. As will be described in more detail below, in one non-limiting embodiment the vent system includes a passage, such as a crescent-shaped vent passage, in flow communication on one end with the control chamber and on the other end with a vent chamber. Flow through a vent outlet for the vent chamber is controlled by a plunger 29 associated with the solenoid 28, which can be moved to open or close the vent outlet. The valve 10 also includes a rotatable stop 30 that can be used to adjust or control the maximum opening position of the valve element.

The valve 10 also includes a swing check retaining ring 302 to retain the valve element 300 in the valve body 14. In the illustrated embodiment, the solenoid 28 is connected to the valve cover 16 by a bleed plug or fitting 90. A manual override lever 304 can be operatively connected to the solenoid 28.

Figure 4:
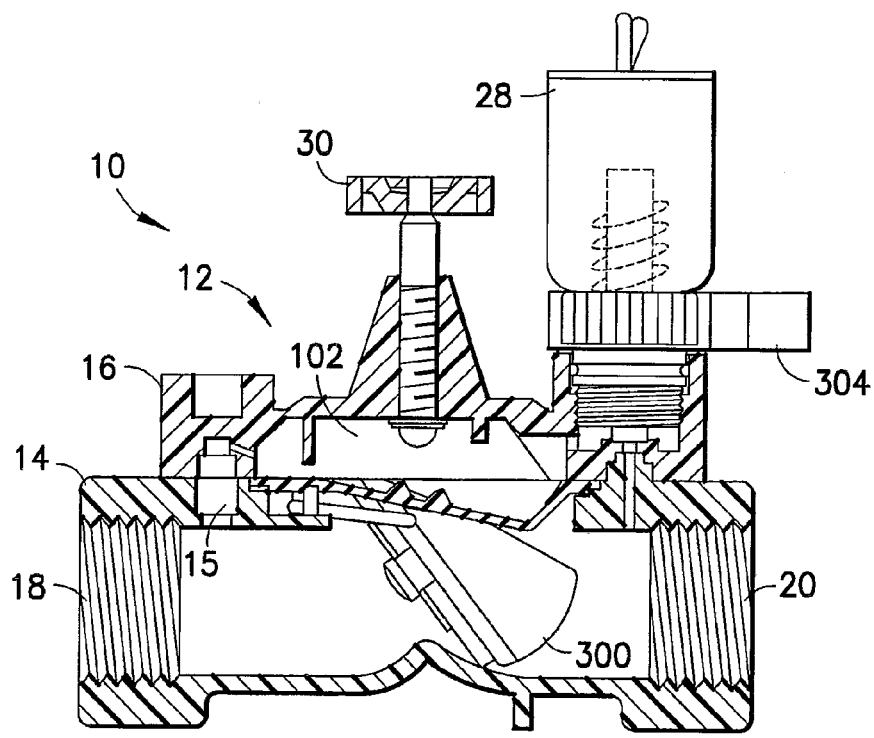
FIG. 4 is a side, sectional view of the valve of FIG. 1 in a closed configuration.
Figure 5:
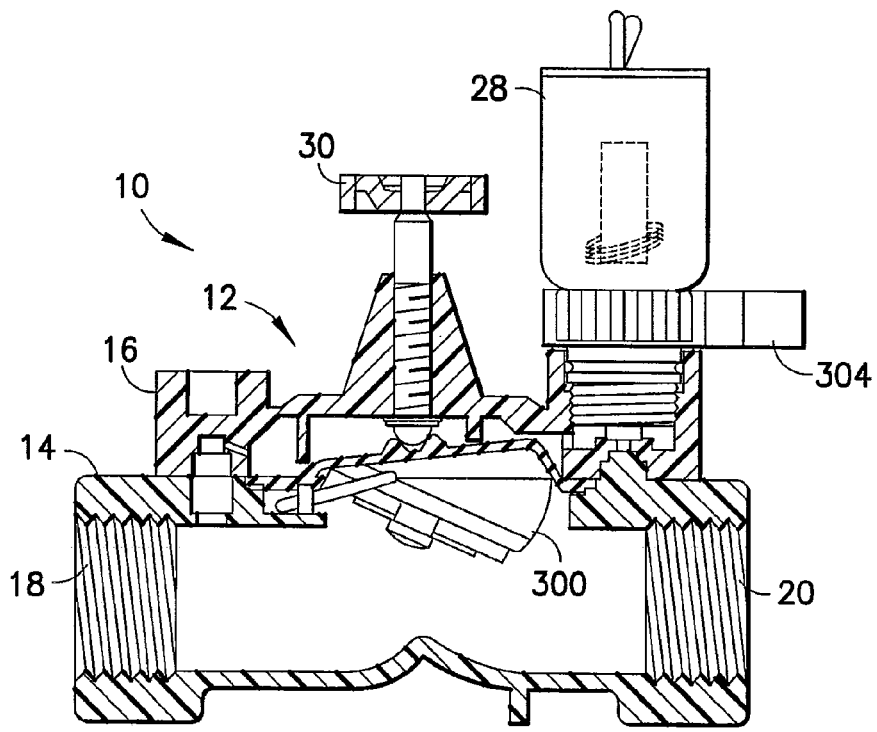
FIG. 5 is a side, sectional view of the valve of FIG. 1 in an open configuration.

FIG. 4 shows the valve 10 in a closed configuration in which the valve element 300 blocks the flow passage, preventing fluid flow through the valve 10. FIG. 5 shows the valve 10 in an open configuration in which fluid can flow from the inlet end 18, through the flow passage, and out the outlet end 20.

The above-described diaphragm valve basic components and their operation will be well understood by one of ordinary skill in the diaphragm valve art and, hence, will not be described in any great detail. Examples of known diaphragm valves and their operation are described, for example, in U.S. Pat. Nos. 4,336,918; 4,301,992; 4,893,645; 4,797,820; 4,477, 051; 4,787,413; 5,853,026; and 6,557,580. However, unlike conventional diaphragm valves, the valve 10 of the invention includes operational elements and/or a relief system in accordance with the invention, as will now be described, which make the valve particularly useful as a flush valve in a waste water system.

Figure 6:
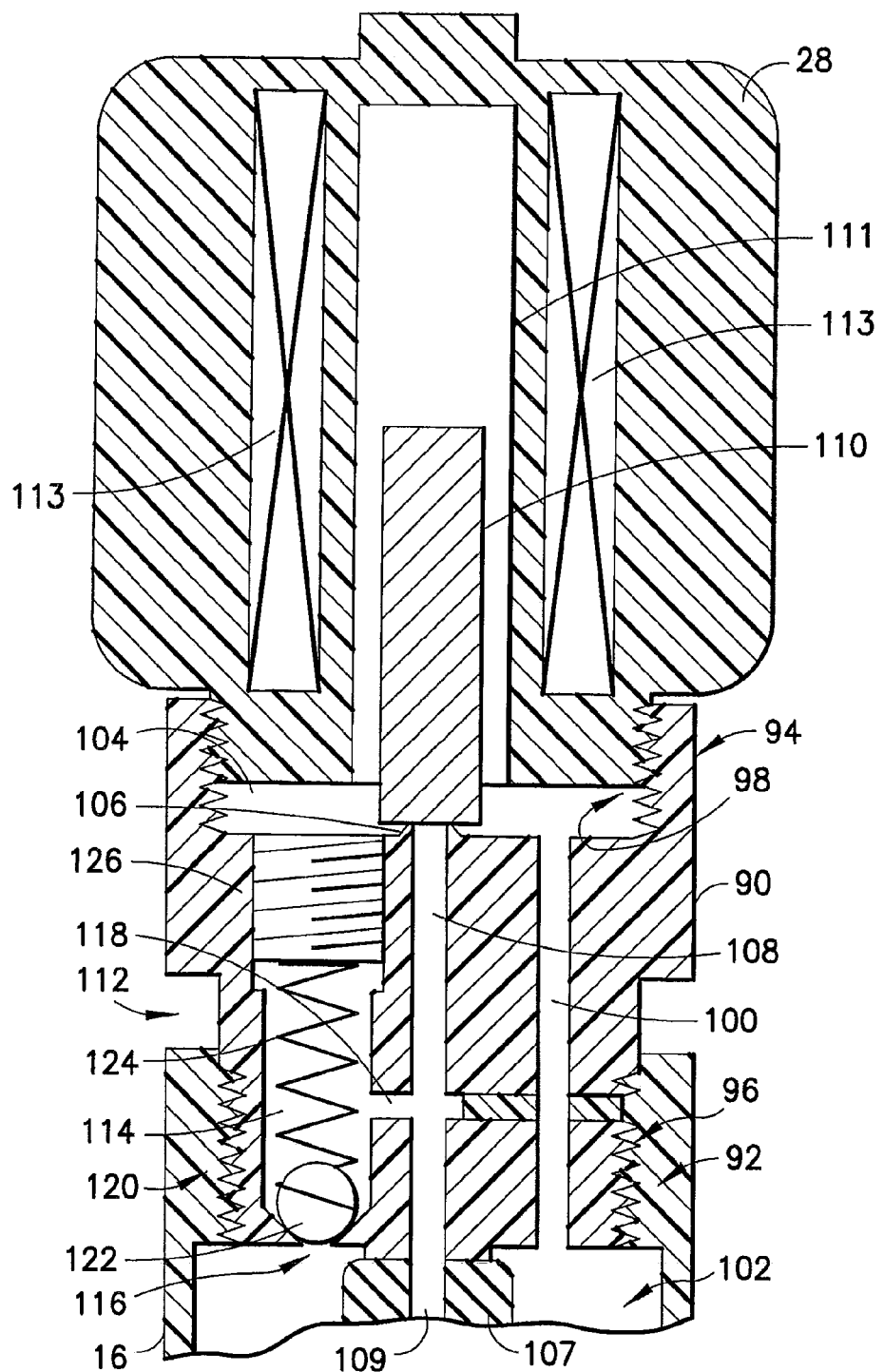
FIG. 6 is a side, cut-away view of a portion of a valve incorporating a valve relief system of the invention.

A portion of the valve 10 of the invention incorporating a mechanical relief assembly is shown in FIG. 6. The bleed plug or fitting 90 has a first end 92 and a second end 94. The first end 92 is connectable with the valve 10, such as with the cover 16, and the second end 94 engages the solenoid 28. In the embodiment illustrated in FIG. 6, the first end 92 of the fitting 90 has external threads 96 configured to engage threads on the cover 16, and the second end 94 has internal threads 98 configured to engage threads on the solenoid 28. The valve 10 has a vent system incorporating a vent inlet passage 100 with one end (lower end) in flow communication with a control chamber 102 and the other end (upper end) in flow communication with a vent chamber 104. A vent valve seat 106 is located in the vent chamber 104 and is in flow communication with a vent outlet conduit 108. When the fitting 90 is engaged with the cover 16, the first end 92 of the fitting 90 contacts a raised sealing member 107. An outlet conduit 109 in the sealing member 107 aligns with the lower end of the outlet conduit 108 in the fitting 90.

Flow through the outlet conduit 108 is controlled by a piston 110 of the solenoid 28. The piston 110 is slidable within a core tube 111 surrounded by a coil 113, as is conventional in many solenoids. As shown in FIG. 6, when the piston 110 is engaged with the vent valve seat 106, flow to the vent outlet conduit 108 is prevented. The fluid pressure in the control chamber 102 is built up to be equal to the fluid pressure of the fluid supply source entering valve 10 through inlet end 18. In particular, fluid flows into valve 10 through inlet end 18, through chamber inlet 15 and into control chamber 102 above diaphragm 26. Control chamber 102 extends across the top of valve 10 over diaphragm 26 and into the portion of valve 10 to which solenoid 28 is threaded thereto. With the piston 110 of solenoid 28 seated on vent valve seat 106, vent chamber 104 is closed from fluid communication across vent valve seat 106, and control chamber 102 is therefore closed as well. The fluid pressure within control chamber 102 applies a force across diaphragm 26, maintaining the diaphragm 26 in an extending position and preventing it from lifting, thereby maintaining the swing check valve 300 in a downward state and preventing swing check valve 300 from lifting, thus preventing fluid flow through the valve 10. When the piston 110 is retracted (i.e., moved upwardly), such as by energizing the coil 113, fluid communication is established between vent chamber 104 and vent outlet 108, thus opening the vent outlet conduit 108 and allowing fluid flow from the vent inlet passage 100, through the vent chamber 104, and out the vent outlet conduit 108 into the outlet end 20 of the valve 10, from where the fluid passes to the fixture associated with valve 10. The vent system is used to bleed pressure from the control chamber 102 to open the main valve element in the valve body 14. This allows the valve element to be opened and closed to control fluid flow through the valve 10.

More particularly, as will be appreciated by one of ordinary skill in the art, the solenoid 28 is connected to a conventional actuator, such as a conventional push-button actuator, to effect actuation of the valve 10 during normal use of the valve 10, such as to effect flushing of an attached fixture. To flush the equipment associated with the valve 10, the actuator is activated. This sends an electrical signal to the coil 113 which energizes the coil 113, thereby causing the piston 110 to lift from the vent valve seat 106. Such movement opens vent valve seat 106 and places vent chamber 104 in fluid communication with vent outlet 108. Thus, fluid flow is established from the control chamber 102, through the vent inlet 100, through vent chamber 104, and out the vent outlet 108, into the outlet end 20 of the valve 10. This relieves the pressure in the control chamber 102, creating a pressure differential across the diaphragm 26 and the main valve element, i.e. the swing check valve 300, in the flow passage, which is pressurized with fluid pressure from fluid flowing from the main water source attached at inlet end 18 of valve 10. This pressure differential effects movement of the swing check valve 300, thereby opening valve 10 for fluid flow between inlet end 18 and outlet end 20. To close the main valve element, the solenoid 28 is disengaged (e.g., the coil 113 is de-energized) such that the piston 110 re-engages the vent valve seat 106 to close the vent outlet 108. Such closure closes off any fluid flow therethrough, thereby allowing fluid, i.e. water, to re-accumulate in vent chamber 104, and re-pressurizing the control chamber 102 above diaphragm 26 and closing swing check valve 300.

Valve 10 of the present invention further incorporates a pressure relief system or assembly in order to prevent the build-up of internal pressure within valve 10 beyond a predetermined threshold limit. In particular, valve 10 is designed for use as a flow control valve in water systems, such as a waste water system. Such water systems involve incoming water flow from a main water system, which may be a city water supply. As such, these water systems are subject to fluctuations in water pressure. In order to prevent damage to the internal operations of the valve from any spikes in water pressure or excessive build up of pressure, valve 10 incorporates a pressure relief system.

The pressure relief system may be incorporated into any portion of the valve 10. In one embodiment, the relief system is incorporated adjacent the solenoid operation of the valve 10. In particular, in one practice of the invention, the valve 10 can incorporate a mechanical relief assembly 112 at fitting 90, as depicted in FIG. 6. In this embodiment, a relief system comprises a relief chamber 114 formed in the fitting 90. This can be done in any conventional manner, such as by drilling or molding a fitting to have the relief chamber 114. The relief chamber 114 includes a relief inlet 116 in flow communication with the control chamber 102 and a relief outlet 118 in flow communication with the vent outlet conduit 108. A mechanical relief device, such as a relief valve 120, is positioned in the relief chamber 114. The relief valve 120 can be of any conventional type. However, in the illustrated embodiment, the relief valve 120 is a ball relief valve having a ball 122 biased by a spring 124. The spring 124 can be connected at an end opposite of the ball to a plug 126 that can be formed in the fitting 90 or can be engaged with the fitting 90 in any conventional manner. For example, the plug 126 can be configured to engage threads formed in the relief chamber 114. Alternatively, the upper end of the relief chamber 114 can be closed, in which case no plug 126 would be required.

The spring 124 is configured such that at fluid pressures below a predefined value, the spring bias pushes the ball 122 against a sealing surface at the relief inlet 116 opening to close the relief inlet 116. However, if the forces applied against the ball 122 based on the fluid pressure applied against the ball 122 at the relief inlet 116 reaches or exceeds the predefined value (based on the bias of the spring 124), the fluid pressure overcomes the bias of the spring 124 to push the ball 122 inwardly to open the relief inlet 116 to prevent fluid flow through the relief assembly 112. As will be appreciated by one skilled in the art, the predefined relief pressure can be changed or adjusted by replacing the spring 124 with another spring of differing spring bias.

In the practice of the invention, the relief assembly 112 prevents over pressurization of the interior of the valve 10 to prevent leakage and/or damage to the valve at high pressures. For example, with reference to FIG. 6, should the pressure in the control chamber 102 meet or exceed a predetermined relief pressure based on the bias of the spring 124, the ball 122 is pushed away from the inlet 116 against the bias of the spring 124 to allow fluid to flow through the inlet 116 and out the relief outlet 118 into the vent outlet 108. When the fluid pressure drops below the preset value for the relief valve 120, the bias of the spring 124 forces the ball 122 to close the inlet 116 to stop any additional fluid flow through the relief assembly 112.

FIG. 7 shows an alternative configuration of a mechanical relief assembly 128 of the invention. In this embodiment, the inlet 116 of the relief chamber 114 is in flow communication with the water source from the control chamber 102 at the vent chamber 104 rather than directly at the control chamber 102. However, the relief assembly 128 would work in a similar manner as the relief assembly 112 described above in that when the pressure in the vent chamber 104 rises above a pre-selected value, the fluid pressure forces the ball 122 downwardly against the bias of the spring to allow fluid to flow out of the relief outlet 118 and into the vent outlet 108, thereby relieving the pressure against the diaphragm 26 to effect movement of the swing check valve 300, thereby opening valve 10 for fluid flow therethrough and relieving the pressure inside valve 10 to protect from damage or leakage.

FIG. 8 is an alternative embodiment of a mechanical relief assembly 130 incorporating features of the invention. In this embodiment, the inlet 116 for the relief chamber 114 is in flow communication with the vent inlet passage 100 such that when pressure in the vent inlet passage 100 rises above the pre-selected level, the relief valve 120 opens and fluid flows from the vent inlet passage 100 through the relief outlet 118 into the vent outlet 108.

FIG. 9 is similar to the configuration shown in FIG. 7 but the spring-biased ball relief is replaced with a compressible plug or member 150 configured to deform at a pre-selected pressure such that when the pressure in the vent chamber 104 reaches the pre-selected pressure, the pressure deforms the compressible member 150 to open the relief outlet 118. In one specific embodiment, the compressible member 150 can be of a durometer selected to provide a selected opening pressure. The material can be, for example, neoprene, rubber, or the like.

Figure 10:
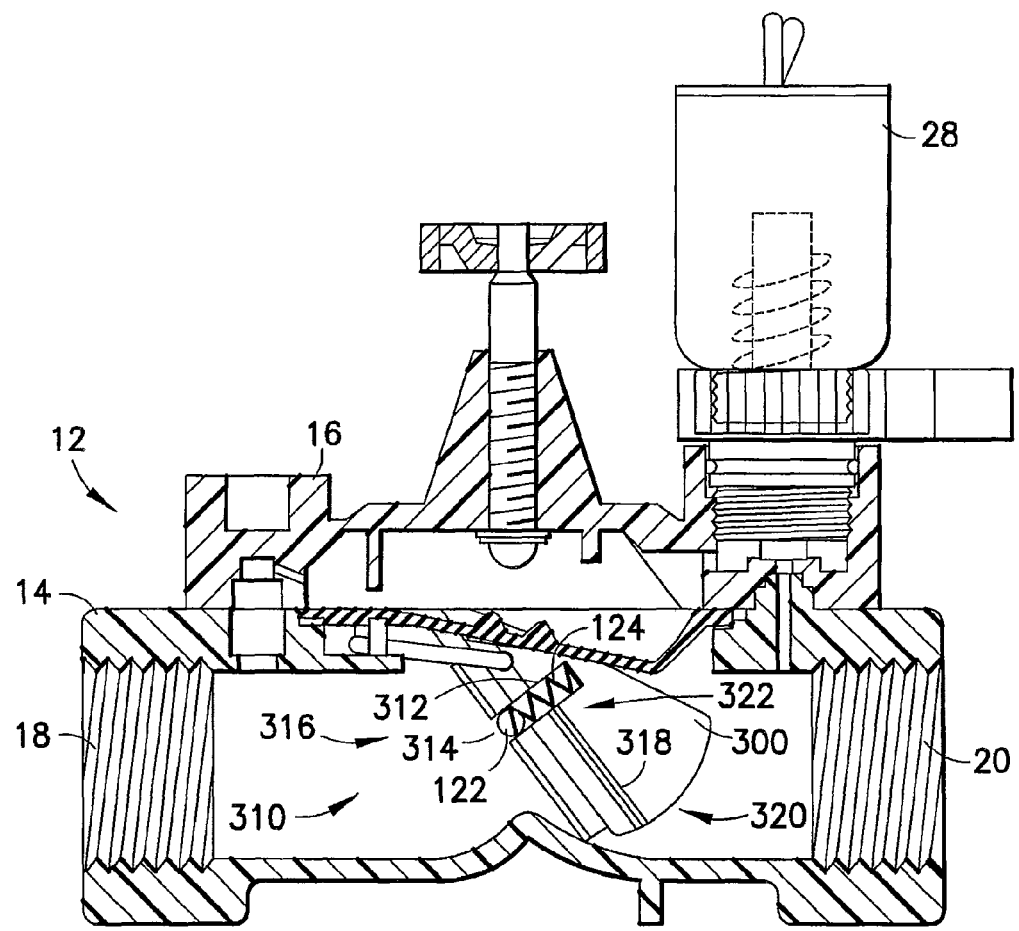
FIG. 10 is a side, sectional view of a valve of the invention having a valve relief system located in the valve body.

A further mechanical relief assembly 310 is shown in FIG. 10. In this embodiment, the relief assembly 310 is formed in a portion of the valve body 14, such as in the valve element 300, rather than in the solenoid 28 as in the embodiments described above. The relief assembly 310 comprises a relief chamber 312 formed in the valve element 300 and having a relief inlet 314 on the inlet side 316 of the valve element 300, i.e., in flow communication with the inlet side of the flow passage. A relief outlet 318 extends between the relief chamber 312 and an outlet side 320 of the valve element 300, i.e., one end of the relief outlet 318 is in flow communication with the relief chamber 312 and the other end of the relief outlet 318 is in flow communication with the outlet side of the flow passage.

A mechanical relief valve 322 (relief device) of any conventional type is located in the relief chamber 312. In the illustrated embodiment, the mechanical relief valve 322 is depicted as a ball relief valve having a ball 122 biased by a spring 124 as described above. The spring 124 is selected or configured such that at fluid pressures on the inlet side 316 of the valve element 300 below a predetermined value, the spring 124 pushes the ball 122 against a sealing surface at the relief inlet 314 to close the relief inlet 314. However, if the fluid pressure on the inlet side 316 of the valve element 300 reaches or exceeds the predetermined value based on the bias of the spring 124, the fluid pressure overcomes the bias of the spring 124 to push the ball 122 inwardly to open the relief inlet 314 and allow fluid flow through the relief chamber 312 and out the relief outlet 318. In this manner, the inlet side of the flow passage is placed in flow communication with the outlet side of the flow passage through the valve element 300 via the relief assembly 310, thereby venting a portion of fluid, i.e., water, therethrough. Once sufficient fluid flow through the relief assembly 310 causes the fluid pressure at the inlet side 316 of the valve to be reduced to a value below the predetermined threshold based on the bias of the spring 124, the spring 124 pushes the ball 122 back to the sealing position, closing off the relief chamber 312 from further fluid flow therethrough. This embodiment prevents over-pressurization of the valve 10 based on bleeding small volumes of water through the valve 10, thereby effectively relieving internal pressure build-up without effecting full opening of the valve element 300, and therefore without fully flushing any fixture associated with the valve 10.

In a further embodiment of the invention, the pressure relief system incorporates an electronic mechanism for detecting pressure within the valve in excess of a predetermined limit, as opposed to (or in addition to) a mechanical mechanism as set forth in the embodiments previously described. In particular, an electronic pressure relief assembly may be incorporated into a portion of valve 10, so as to effectively measure to water pressure within valve 10, such as within control chamber 102, to prevent a build up of excessive pressure therein. Desirably, such an electronic pressure relief system may be incorporated into a portion of the valve adjacent other electronically operated features of the valve, such as adjacent to or integrated with the solenoid portion of the valve. In this manner, a conventional valve such as that disclosed in FIG. 1 above or such as disclosed U.S. Pat. No. 4,336,918 can be easily modified and retrofitted by replacing a conventional solenoid operator with a modified solenoid incorporating an electronic relief assembly as disclosed in the present invention.

Figure 11:
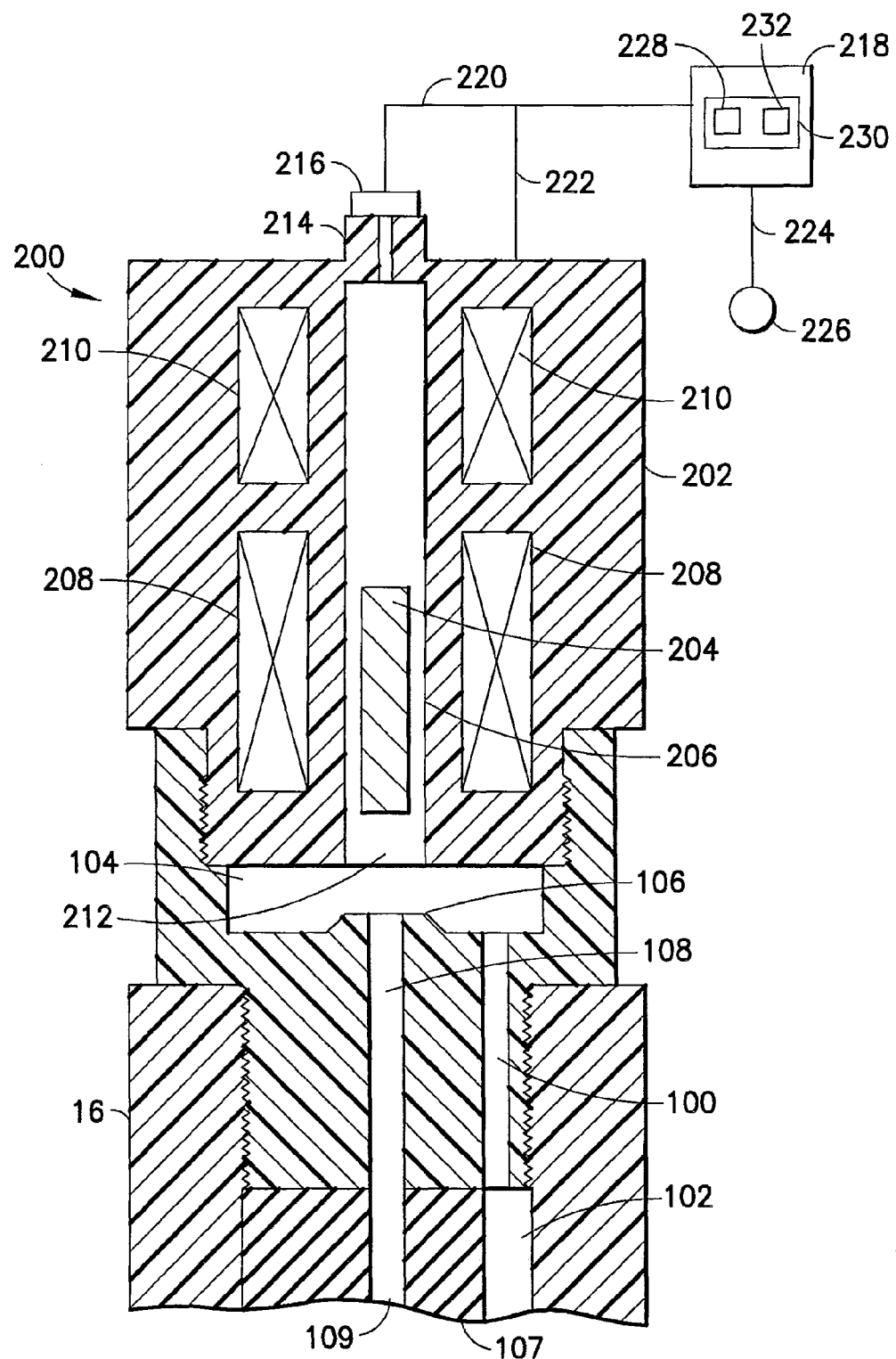
FIG. 11 is a side, cut-away view (not to scale) of an alternative valve relief system of the invention.

For example, a portion of a valve 10 incorporating an electronic relief assembly 200 in accordance with a further embodiment is shown in FIG. 11. In this embodiment, a modified solenoid 202 is utilized. The solenoid 202 engages the plug or fitting 90, for example as described above with respect to FIG. 6. The solenoid 202 includes a piston 204 slidable within a core tube 206. A coil surrounds at least a portion of the core tube 206. The coil can be a single coil 113 as described above or, in the illustrated embodiment, the coil can comprise a first coil section 208 and a second coil section 210. The first coil section 208 is located at or near the bottom or open end 212 of the core tube 206. The second coil section 210 is located at or near the top or closed end 214 of the core tube 206.

In this electronic relief assembly 200, a pressure transducer 216 is connected to the solenoid 202 and is configured to measure the fluid pressure within the valve, e.g., in the vent chamber 104, which is in fluid communication with the control chamber 102. For example, in one embodiment the pressure transducer 216 can be configured to extend into the vent chamber 104. Alternatively, in the embodiment shown in FIG. 11, the pressure transducer 216 can be connected to the top 214 of the core tube 206 and can extend into the interior of the core tube 206. As will be appreciated by one skilled in the art, a gap exists between the outside diameter of the piston 204 and the inside diameter of the core tube 206 such that fluid in the vent chamber 104 flows into the core tube 206 around the piston 204. Thus, the pressure in the core tube 206 should be substantially the same as that in the vent chamber 104 and the control chamber 102. The pressure transducer 216 is in electronic communication with a control board 218 in any conventional manner, such as by one or more wires or cables 220. The control board 218 can be, for example, a conventional 4IO or 8IO control board, as is known to those of ordinary skill in the art. The control board 218 is connected to an electrical power source to provide electrical power to the solenoid 202 in any conventional manner, such as by one or more cables 222. The control board 218 is in electronic communication, such as by a wire or cable 224, with an actuator 226, such as a conventional push button or similar actuator.

The relief assembly 200 in the embodiment of FIG. 11 operates as follows in one non-limiting embodiment. The pressure transducer 216 senses the static fluid pressure inside the core tube 206. By "static pressure" is meant the fluid pressure when the solenoid 202 is de-energized, that is, when the piston 204 engages the valve seat 106. The system can be configured such that a pressure range sensed by the pressure transducer 216 can correspond to an output signal of the transducer 216. For example, a pressure range of 0 to 150 psi can correspond to an output signal of 0 to 5 volts DC. A high-voltage threshold can be predetermined, which corresponds to a relief pressure for the relief assembly 200. By "relief pressure" is meant the fluid pressure at which the relief assembly 200 is activated. The static pressure can be monitored either continuously or intermittently by a microprocessor 228 associated with a pressure transducer control 230 on the control board 218. Depending upon the output signal of the pressure transducer 216, an amplifier 232 can also be present on the control board 218 to boost the output signal from the pressure transducer 216, if needed. In any event, when the high-voltage threshold is detected (i.e., the relief pressure is attained), the microprocessor 228 sends a signal to energize the solenoid 202.

In one embodiment, the solenoid can be energized for a predetermined period of time, for example, in the range of 1 to 3 seconds. This lifts the piston 204 off of the valve seat 106 for that predetermined period of time to open the vent outlet 108 for fluid flow therethrough, thereby releasing a portion of the fluid within vent chamber 104 and control chamber 102, and lowering the pressure within the vent chamber 104 and control chamber 102. After this predetermined period of time, the solenoid 202 is de-energized such that the piston 204 again engages the valve seat 106. The pressure transducer 216 may thereafter again senses the static pressure inside the core tube 206. If the static pressure as measured within vent chamber 104 is still above the relief pressure (that is, the output signal of the pressure transducer 216 is at or above the high-voltage threshold), the microprocessor 228 again activates the solenoid 202 for a predetermined period of time to lift the piston 204 to again open the vent outlet 108 for fluid flow therethrough, relieving at least some of the fluid pressure within the vent chamber 104 and control chamber 102. This cycle can continue until the static pressure sensed by the pressure transducer 216 is below the predetermined relief pressure.

In a further embodiment, operation of the solenoid to relieve the pressure within valve 10 is not necessarily based on a predetermined time value for venting a specified volume of fluid out of vent chamber 104 and control chamber 102, but is instead based on the internal pressure within valve 10 during the venting as measured by the pressure transducer 216. For example, when the high-voltage threshold is attained (i.e. the relief pressure is attained based on the measurement from the pressure transducer 216), the solenoid 202 is activated to lift the piston 204 and relieve the pressure, and the solenoid 202 remains energized. In this embodiment, the pressure transducer 216 continues to monitor the internal fluid pressure within the core tube 111 and/or the vent chamber 104 while the solenoid 202 is energized. The solenoid 202 remains energized until the pressure transducer 216 senses a closing voltage threshold, i.e., a voltage associated with a predefined fluid pressure at which the solenoid 202 is to be de-energized. The closing voltage threshold corresponds to a voltage output corresponding to a dynamic fluid pressure defined as the closing pressure. By "dynamic fluid pressure" is meant the fluid pressure in the core tube 111 and/or vent chamber 104 while the solenoid 202 is energized, that is while the piston 204 is off of the valve seat 106 and fluid is flowing through the vent chamber 104 and out the vent outlet 108. For example, the microprocessor 228 may be programmed such that a closing voltage threshold may correspond to a specific pressure within the vent chamber 104, such as a voltage threshold of 3.2V DC corresponding to 100 psi, representing an acceptable internal pressure to prevent damage within valve 10. When the dynamic fluid pressure measured by pressure transducer 216 reaches the acceptable threshold corresponding to the closing voltage threshold, the microprocessor 228 de-energizes the solenoid 202 to cause the piston 204 to move downwardly to re-engage the valve seat 106 and seal off the vent outlet 108.

As will be appreciated by one skilled in the art, the above relief methods may allow sufficient fluid flow through out of vent chamber 104 and control chamber 102 through vent outlet 108 to cause a sufficient drop in pressure within control chamber 102 which would release diaphragm 26, thereby opening the main valve element 300 of valve 10. As such, the equipment or fixture associated with the flush valve 10, such as a commode or urinal, would be caused to flush when the piston 204 is lifted from the valve seat 106 to relieve the fluid pressure. The invention, however, further provides embodiments which effectively release the pressure within valve 10 without necessarily dropping the pressure of control chamber 102 below the required threshold to maintain diaphragm 26 closed, thereby preventing operation of valve 10.

For example, it is contemplated that in a single coil system such as that described above, the microprocessor may be programmed differently depending on whether a normal flush request from actuator 226 is received or whether a high voltage threshold is detected based on a signal from the pressure measured by the pressure transducer 216. If the equipment is to be flushed such as based on receipt of a normal flush request from actuator 226, the microprocessor 228 sends a signal to energize the solenoid to lift the piston 204 off of the valve seat 106 to open the vent outlet 108 for venting of control chamber 102 for a sufficient period of time typically associated with operation of the valve 10, in order to effect opening of the valve element of the valve 10 and to flush the associated fixture or equipment, such as for a period of more than 3 seconds. On the other hand, when a high voltage threshold is detected based readings from the pressure transducer 216, the microprocessor 228 can send a signal to energize the solenoid for only a limited predetermined period of time below that which is normally associated with release of the control chamber 102 which would effect opening of the valve 10, such as a period of less than 1 second. In this manner, the pressure can be effectively released within valve 10 without effecting a full flush of the fixture associated with the valve 10.

Alternatively, the illustrated embodiment of FIG. 11 utilizes a two-part coil to prevent complete opening of valve 10 to prevent flushing of the associated equipment. For example, if the equipment is to be flushed such as based on receipt of a normal flush request from actuator 226, the upper or second coil section 210 can be energized to lift the piston 204 off of the valve seat 106 to open the vent outlet 108 for a sufficient period of time typically associated with venting of control chamber 102 for operation of the valve 10, in order to effect opening of the valve element of the valve 10 and to flush the associated fixture or equipment. However, if a pressure above the high-voltage threshold is detected by the pressure transducer 216, the microprocessor 228 activates only the lower coil 208 to slightly lift the piston 204 off of the valve seat 106 for a brief period of time, e.g., less than 1 second. If the piston 204 is lifted only for a short period of time and/or is lifted only slightly off of the valve seat 106 in order to lower the pressure in the vent chamber 104, flushing of the associated equipment may be prevented.

Under normal operation, when the valve 10 is to be opened to permit flushing of an associated component, the actuator 226 is actuated, such as by pressing a button. Upon receiving the actuation signal, the control board 218 sends a signal via the cable 222 to the solenoid 202 to energize the coils (113 or 210) to lift the piston 204 off of the valve seat 106. This vents the fluid in the vent chamber 104 through the vent outlet 108, thereby venting the control chamber 102 and opening the valve element 300 of the valve 10. In one practice of the invention, when the actuation signal is received, the microprocessor 228 determines the static fluid pressure inside the core tube 206 by the pressure transducer 216. Based on this sensed static pressure, the microprocessor 228 calculates a flush time in order for the valve 10 to deliver a desired quantity of water. The microprocessor 228 actuates the solenoid 202 to lift the piston 204 for a predetermined specific period of time such that the valve 10 provides a predetermined quantity of fluid. For example, if a total volume of fluid flow through the valve 10 is desired to be 1.6 gallons and the sensed static pressure is 60 psi, the microprocessor 228 can actuate the solenoid 202 for a first predetermined period of time corresponding to a flow through the valve 10 of 1.6 gallons. However, if the sensed static pressure is 50 psi, the microprocessor 228 would actuate the solenoid 202 for a second predetermined period of time greater than the first predetermined period of time in order to provide the same amount of water through the valve 10.

In another aspect of the invention, the pressure transducer 216 can be adapted to monitor the dynamic fluid pressure during operation of the valve to control the amount of water flow through valve 10. For example, the precise volume of fluid flow through valve 10 for a given period of time can be calculated based on the interior volume of valve 10, the time of flow through valve 10 and the fluid pressure of the water flowing through valve 10. For a given fluid pressure, it can be calculated that the operating time for valve 10 may be a certain period of time for a given flow volume. For example, it may be known based on normal line pressure from the water source through inlet 18 that valve 10 should remain open for a specified period of time (based on operation of solenoid 202), such as 3 seconds, to effect a specified flow volume, such as 1.6 gallons per flush. The line pressure from the water source, however, may fluctuate depending on a number of factors, such as multiple fixtures attached to the water source operating simultaneously. By monitoring the dynamic fluid pressure within the valve 10 during operation of the valve, such as through the pressure transducer 216, the operating time of the valve can be adjusted during operation of the valve 10 so as to ensure that the desired flow volume is achieved through the valve 10.

For example, when the actuation signal is received from the actuator 226, the microprocessor 228 can send signal the pressure transducer 216 to sense the static pressure of the fluid within valve 10, such as in the core tube 206. Based upon this sensed static pressure, an initial actuation time for the solenoid 202 to provide a predetermined volume of water through the valve 10 is determined. This initial actuation time for solenoid 202 can be pre-calculated based upon the sensed pressure when applied with the known interior volume of valve 10 and the desired amount of water flow therethrough. In this embodiment, the pressure transducer 216 continues to monitor the dynamic fluid pressure in the core tube 206 during valve actuation and operation. If this dynamic fluid pressure varies during the flushing cycle, the microprocessor 228 adjusts the actuation time of the solenoid 202 in order to compensate for fluid pressure variation, to ensure that the desired volume of flushing water is delivered through valve 10.

For example, a desired flow volume, such as 1.6 gallons per flush, is required when a normal flush request is received. Based upon the initial static pressure measurement, the microprocessor calculates the initial operating time for solenoid 202 to ensure that valve 10 remains open for the calculated operating time. For example, if based upon the initial static pressure measurement a flush time of 3 seconds is determined by the microprocessor 228 to correspond to a desired total volume through the valve 10, such as 1.6 gallons per flush, the solenoid 202 is actuated for the determined time period. However, if during this flushing process the dynamic fluid pressure sensed by the pressure transducer 216 varies from a predetermined value or range, such as by increasing or decreasing from the initial static pressure beyond a predetermined amount, the microprocessor 228 recalculates the amount of time the solenoid 202 needs to be activated in order to maintain valve 10 open for an appropriate time to ensure that the desired volume flow therethrough is achieved, such as a discharge volume of 1.6 gallons from the valve 10. This ensures a desired amount of fluid is discharged from the valve 10 even if the fluid pressure varies during the operation of the valve 10 such as during the flushing process. That is, knowing the initial pressure, the dynamic pressure, and the flow rate through the valve 10 at the dynamic pressure, the microprocessor 228 can determine an actual flush time needed to flush a desired amount of water through the valve 10. In this manner, the effective flushing volume of valve 10 will remain constant over the life of valve 10, regardless of wearing of the internal components of valve 10, which can alter the effective flushing volume of conventional diaphragm valves over time.

Figure 12:
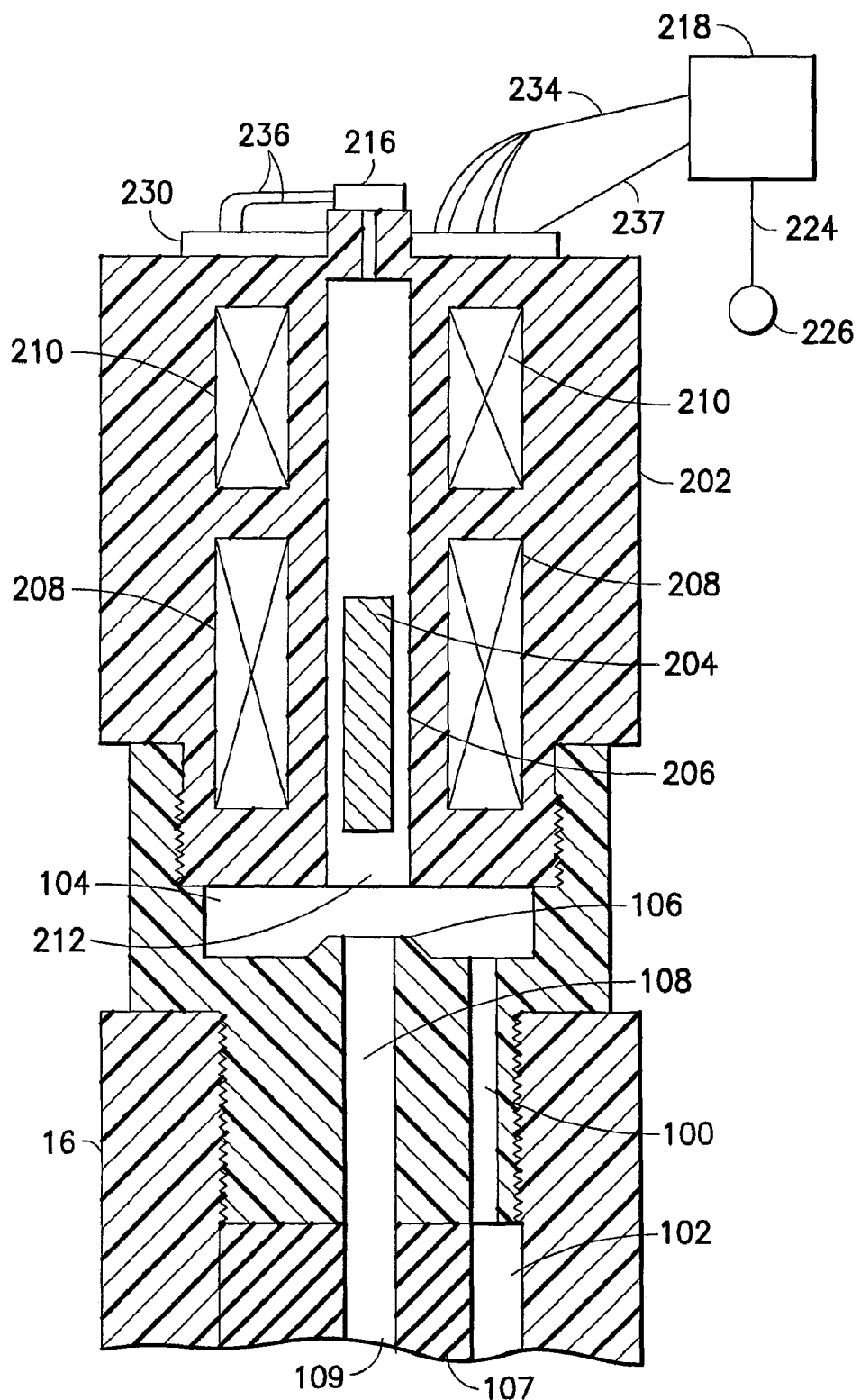
FIG. 12 is a side, cut-away view (not to scale) of another valve system incorporating features of the invention.

In the embodiment shown in FIG. 12, the pressure transducer control 230 is located on the valve 10, such as on the solenoid 202. The pressure transducer control 230 is connected to the main control board 218 in any conventional manner, such as by a cable 234 having one or more wires. The pressure transducer 216 is connected to the pressure transducer control board 230 in any conventional manner, such as by cables or wires 236. The control board 218 can provide electrical power to the transducer control board 230 and/or solenoid 202, such as by a cable 237, such that the relief function and flush function as described above can be maintained.

Figure 13:
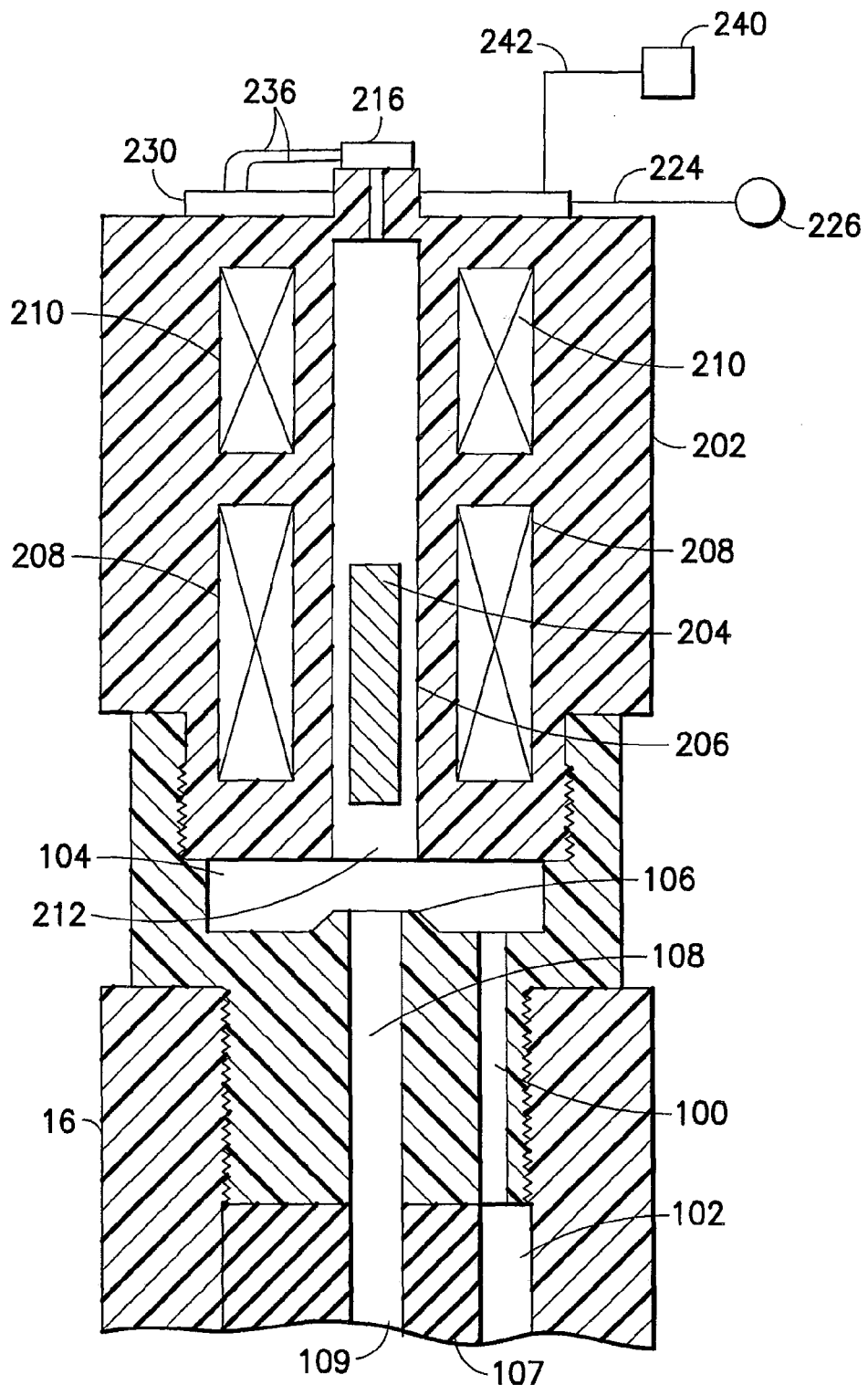
FIG. 13 is a side, cut-away view (not to scale) of a further valve system of the invention.

In the embodiment, shown in FIG. 13, the main control board 218, which includes the pressure transducer control 230 and associated microprocessor 228 and amplifier 232, is located directly on the valve 10, such as on the solenoid 202. A power source 240, such as a conventional wall outlet or a battery, is in electronic communication with the main control board 218 and/or solenoid 202 in conventional manner, such as by a cable 242. The actuator 226 is connected to the main control board 218 on the solenoid 202. The flushing and/or relief actions occur in similar manner as described above.

In the electronic relief systems described above, electrical power can be continually provided to the pressure transducer 216 such that the transducer 216 continually monitors the fluid pressure within the valve 10. However, in an alternate embodiment, electrical power may be supplied to the pressure transducer 216 to effect monitoring at a specific time only, such as when the actuator 226 is activated. When the actuator 226 is activated, the microprocessor 228 sends power to the transducer 216 to sense the static fluid pressure. Based upon this static pressure, a flush time (i.e., solenoid activation time) is calculated to achieve a desired flush volume. The transducer 216 can remain powered during the flush to monitor the dynamic fluid pressure and adjust the flush time as described above. Moreover, the microprocessor 228 may be programmed to supply power to the pressure transducer 216 at intermittent time periods, such as every 10 minutes, to intermittently monitor the internal pressure within valve 10.

It is further contemplated that the pressure monitoring function of the transducer 216 may be utilized as a maintenance function for valve 10. For example, the internal components of diaphragm valves typically wear over time, which can result in prolonged fluid flow therethrough, wasting water. Oftentimes, such wearing causes the valve to take a longer period of time in order to reseal the diaphragm based upon the time required to build up water pressure within the valve 10 at the inlet side of the diaphragm 26. The pressure transducer 216 may be programmed to detect the water pressure within valve 10 after a certain period of time after a normal flush as requested and effected. The typical range of time required to achieve the water pressure necessary to effect resealing of diaphragm 26 and closure of the valve 10 is known based on normal operation of the valve 10. A comparison of the water pressure after a normal flush at the known time period can provide information regarding the wear of the valve. For example, if the water pressure detected after the predetermined time period is lower than the typical water pressure value as known, valve 10 may require servicing or replacement. A signal including this information could be transmitted to a central processing unit, which could then alert the maintenance staff that servicing is required.

It will be readily appreciated by those skilled in the art that modifications may be made to the invention without departing from the concepts disclosed in the foregoing description. For example, various components of the mechanical and electronic relief devices described above can be used together in the same valve. Accordingly, the particular embodiments described in detail herein are illustrative only and are not limiting to the scope of the invention, which is to be given the full breadth of the appended claims and any and all equivalents thereof.

What is claimed is:

1. A flush valve for a waste water system, comprising:
a valve body comprising a fluid inlet and a fluid outlet and a main valve element extending between the fluid inlet and the fluid outlet, the main valve element adapted for movement to allow fluid flow between the fluid inlet and the fluid outlet based on a pressure differential across a portion of the main valve element;
a vent system comprising a control chamber in flow communication with the fluid inlet of the valve body and a vent outlet in flow communication with the fluid outlet of the valve body;
a solenoid having a piston operable in a core tube in flow communication with the control chamber and configured to open to establish flow communication between the control chamber and the vent outlet thereby venting fluid from the control chamber to the fluid outlet and establishing a pressure differential across a portion of the main valve element and permitting the main valve element to open for fluid flow between the fluid inlet and fluid outlet of the valve body, and to close to prevent fluid communication between the control chamber and the vent outlet to close the main valve element; and
a pressure sensor adapted to sense the fluid pressure of fluid within the core tube, wherein the solenoid is controlled to vent the control chamber for a period of time short enough to reduce the fluid pressure within the control chamber without opening the main valve element when the pressure within the core tube exceeds a predetermined pressure threshold.

2. The flush valve according to claim 1, wherein at least a portion of the valve body is constructed of a plastic material.

3. The flush valve according to claim 1, wherein the vent system further comprises a vent chamber in flow communication with the control chamber through a vent inlet passage extending between the control chamber and the vent chamber, and wherein the vent outlet is in flow communication with the vent chamber.

4. The flush valve according to claim 1, wherein the pressure sensor comprises a pressure transducer.

5. The flush valve according to claim 4, wherein the pressure transducer is connected to a control board comprising a pressure transducer control and a microprocessor.

6. The flush valve according to claim 5, wherein the control board is located on the solenoid.

7. The flush valve according to claim 5, wherein the pressure transducer control includes a voltage amplifier.

8. The flush valve according to claim 1, wherein the core tube is in flow communication with a vent chamber which is in flow communication with the control chamber.

9. The flush valve according to claim 8, including an actuating coil around at least a portion of the core tube.

10. The flush valve according to claim 9, wherein the actuating coil comprises a first coil section and a second coil section.

11. A method of controlling a flush valve, comprising:
providing a flush valve as claimed in claim 1;
defining a pressure threshold corresponding to a relief pressure for the valve;
sensing the fluid pressure of fluid within the valve;
activating the solenoid when the fluid pressure within the valve meets or exceeds the defined pressure threshold.

12. A method of regulating pressure within a flush valve in a waste water system, comprising:
providing a valve body including a fluid inlet and a fluid outlet and a main valve element adapted for movement to allow fluid flow between the fluid inlet and the fluid outlet based on a pressure differential across a portion of the main valve element, the valve comprising a vent system for venting fluid from the fluid inlet to the fluid outlet to establish a pressure differential across a portion of the main valve element to cause the main valve element to open, the vent system comprising a control chamber in flow communication with the fluid inlet of the valve body, a vent outlet in flow communication with the fluid outlet of the valve body, and an electronically operated solenoid having a piston configured to open and close the vent outlet upon energization thereof;
sensing the fluid pressure of fluid within the vent system of the valve;
venting fluid within the vent system of the valve from the fluid inlet to the fluid outlet when the fluid pressure within the vent system exceeds a predetermined pressure threshold corresponding to a relief pressure for the valve, wherein the venting step comprises energizing the solenoid to open the vent outlet to establish flow communication between the control chamber and the vent outlet to vent fluid from the control chamber to the fluid outlet; and
energizing the solenoid for a period of time below that required to vent a volume of fluid from the vent chamber associated with establishing a pressure differential across a portion of the main valve element which would cause the main valve element to open, thereby reducing the fluid pressure within the vent chamber without opening the main valve element.

* * * * *